United States Patent
Nishizawa et al.

(10) Patent No.: US 10,525,681 B2
(45) Date of Patent: Jan. 7, 2020

(54) COMPOSITE MATERIAL AND METHOD OF PRODUCING COMPOSITE MATERIAL

(71) Applicant: TOHOKU UNIVERSITY, Sendai-shi, Miyagi (JP)

(72) Inventors: Matsuhiko Nishizawa, Sendai (JP); Kuniaki Nagamine, Sendai (JP)

(73) Assignee: TOHOKU UNIVERSITY, Sendai-shi, Miyagi (JP)

( * ) Notice: Subject to any disclaimer, the term of this patent is extended or adjusted under 35 U.S.C. 154(b) by 0 days.

(21) Appl. No.: 15/764,456

(22) PCT Filed: Sep. 30, 2016

(86) PCT No.: PCT/JP2016/079880
§ 371 (c)(1),
(2) Date: Mar. 29, 2018

(87) PCT Pub. No.: WO2017/057782
PCT Pub. Date: Apr. 6, 2017

(65) Prior Publication Data
US 2018/0281366 A1 Oct. 4, 2018

(30) Foreign Application Priority Data
Sep. 30, 2015 (JP) ................................. 2015-194485

(51) Int. Cl.
| | |
|---|---|
| *A61B 5/04* | (2006.01) |
| *H01L 29/43* | (2006.01) |
| *H01L 29/51* | (2006.01) |
| *B32B 5/18* | (2006.01) |

(Continued)

(52) U.S. Cl.
CPC .............. *B32B 27/308* (2013.01); *A61B 5/04* (2013.01); *B32B 5/18* (2013.01); *B32B 7/10* (2013.01); *B32B 27/00* (2013.01); *B32B 27/16* (2013.01); *B32B 27/26* (2013.01); *B32B 27/306* (2013.01); *C08F 2/44* (2013.01); *C08F 2/48* (2013.01); *H01L 29/43* (2013.01); *H01L 29/51* (2013.01); *B32B 2260/046* (2013.01); *B32B 2266/122* (2016.11); *B32B 2305/026* (2013.01); *B32B 2307/202* (2013.01); *B32B 2307/206* (2013.01); *B32B 2457/04* (2013.01)

(58) Field of Classification Search
CPC ......... B32B 7/10; H01L 29/43–29/518; A61B 5/04–5/0496
See application file for complete search history.

(56) References Cited

U.S. PATENT DOCUMENTS

2004/0199250 A1* 10/2004 Fell ..................... A61F 2/30767
623/14.12

FOREIGN PATENT DOCUMENTS

| JP | 2008260272 A | 10/2008 |
|---|---|---|
| JP | 2009051211 A | 3/2009 |

(Continued)

OTHER PUBLICATIONS

Machine translation of JP 2009-051211A (Year: 2009).*
(Continued)

*Primary Examiner* — Ramsey Zacharia
(74) *Attorney, Agent, or Firm* — Kenja IP Law PC (57) ABSTRACT

A composite material including a substrate, a porous body provided on the substrate, and insulating polymers starting from a surface of the substrate and extending inside the porous body, and a method of producing the composite material.

8 Claims, 6 Drawing Sheets

(51) Int. Cl.
    *B32B 27/24*     (2006.01)
    *B32B 27/16*     (2006.01)
    *B32B 27/30*     (2006.01)
    *C08F 2/44*     (2006.01)
    *B32B 27/00*     (2006.01)
    *C08F 2/48*     (2006.01)
    *B32B 7/10*     (2006.01)
    *B32B 27/26*     (2006.01)

(56) References Cited

FOREIGN PATENT DOCUMENTS

| | | |
|---|---|---|
| JP | 2013500717 A | 1/2013 |
| JP | 2013060505 A | 4/2013 |
| WO | 2014157550 A1 | 10/2014 |

OTHER PUBLICATIONS

Apr. 3, 2018, International Preliminary Report on Patentability issued in the International Patent Application No. PCT/JP2016/079880.

Jan. 10, 2017, International Search Report issued in the International Patent Application No. PCT/JP2016/079880.

Masato Sasaki et al., "Highly Conductive Stretchable and Biocompatible Electrode—Hydrogel Hybrids for Advanced Tissue Engineering", Advanced Healthcare Materials, 2014, vol. 3, Issue 11.

Jul. 16, 2019, Notification of Reasons for Refusal issued by the Japan Patent Office in the corresponding Japanese Patent Application No. 2015-194485.

\* cited by examiner

FIG. 5A — Collagen hydrogel

FIG. 5B — PPEGDA hydrogel

FIG. 6 — Polypropylene film / PPEGDA hydrogel

FIG. 7

COMPOSITE MATERIAL AND METHOD OF PRODUCING COMPOSITE MATERIAL

TECHNICAL FIELD

This disclosure relates to a composite material and a method of producing composite material.

BACKGROUND

It has been a generalized method of diagnosis and treatment in medical practice to, with various equipments, measure electrical signals from a living body such as performing an electrocardiogram, electromyogram or electroencephalogram, and apply electric current (electrostimulation) to control functions of a living body. Such method uses an electrode, which is a part of the equipment, as an interface between the equipment and the living body.

The electrode used in the medical field generally includes electrically conducting wiring e.g. metal or carbon, and non-electrically conducting substrate material (e.g. plastic or glass). The electrode to be directly contact with a living body requires biocompatibility, and equipments being used nowadays still leave much to be improved in this respect.

Recently, researchers have noticed the merit of using a hydrogel, which is excellent in biocompatibility, in the substrate, and have started to develop techniques of adhering a hydrogel to an electrode material.

A known example of the adhesive technique is to place a hydrogel on an electrode material and perform electrolytic polymerization of conductive polymer to make the conductive polymers extend from the surface of the electrode material to the vicinity of the electrode material, thereby forming a conductive adhesive layer (see WO 2014/157550 (PTL 1) and M. Sasaki, et al., Advanced Healthcare Materials, 2014, 3, 1919. (NPL 1)). These documents report that polymer chains constituting the hydrogel intertwine with the conductive polymers, and in this way the electrode material and the hydrogel are firmly adhered together.

CITATION LIST

Patent Literature

PTL 1: WO 2014/157550

Non-Patent Literature

NPL 1: M. Sasaki, et al., Advanced Healthcare Materials, 2014, 3, 1919.

SUMMARY

Technical Problem

However, in these conventional methods of producing composite material, a gel is adhered to an electrode via polymers, and the polymers are synthesized through electrolytic polymerization. Therefore, it is only a conductive polymer layer that can be provided on the surface layer of the gel of the composite material. From the perspective of device application, adhesion realized by an insulating polymer layer to the surface layer of a porous body such as a gel also has great industrial significance.

Therefore, we aim to realize the synthesis of polymers between a substrate and a porous body even when the polymers are low-conductive polymers, and to provide a composite material where a substrate and a porous body are firmly adhered via insulating polymers.

Solution to Problem

The primary features of this disclosure are as described below.

The presently disclosed composite material includes a substrate, a porous body provided on the substrate, and insulating polymers starting from a surface of the substrate and extending inside the porous body.

The insulating polymers of the presently disclosed composite material preferably have a conductivity of less than 1 mS/cm.

The insulating polymers of the presently disclosed composite material are preferably at least one selected from the group consisting of polyacrylamide, poly(N,N-dimethylacrylamide), PPEGDA and PPEGDM. Additionally, the porous body of the presently disclosed composite material is preferably a hydrogel. Furthermore, the hydrogel of the presently disclosed composite material is preferably at least one selected from the group consisting of collagen, glucomannan, fibrin, alginic acid, polyvinyl alcohol, PPEGDA, PPEGDM, polyhydroxyethylmethacrylate, polyvinylpyrrolidone, polyacrylamide, poly(N,N-dimethylacrylamide), poly(N-isopropylacrylamide), silicone, DN hydrogel and mixtures of at least two of these.

The presently disclosed method of producing composite material includes: introducing polymerization initiators to a surface of a substrate; impregnating monomers into a porous body; and performing polymerization to carry out a polymerization reaction of the monomers with the polymerization initiators being a polymerization starting point.

The polymerization reaction of the monomers in the presently disclosed method of producing composite material is preferably a radical polymerization reaction. Additionally, the polymerization of the monomers in the presently disclosed method of producing composite material preferably starts with at least one selected from the group consisting of thermal reaction, photoreaction, and oxidation-reduction reaction.

Advantageous Effect

The present disclosure can provide a composite material where a substrate and a porous body are firmly adhered via insulating polymers.

BRIEF DESCRIPTION OF THE DRAWINGS

In the accompanying drawings:

FIGS. 4A-4C are photographs when observing a composite material, which is obtained by adhering a DN hydrogel to a PEDOT·PU/PU-Irgacure film, with the naked eye or with an inverted microscope, where FIG. 4A is a photograph when observing the composite material with an inverted microscope, FIG. 4B is a photograph when observing the composite material with the naked eye, (i) of FIG. 4C is a photograph when observing the composite material, which is swollen with phosphate buffer solution, with the naked eye, and (ii) of FIG. 4C is a photograph when observing the composite material, which is dry, with the naked eye;

DETAILED DESCRIPTION

The following describes embodiments of the presently disclosed composite material and the presently disclosed method of producing composite material in detail with reference to the drawings.

(Composite Material)

Figure 1A:
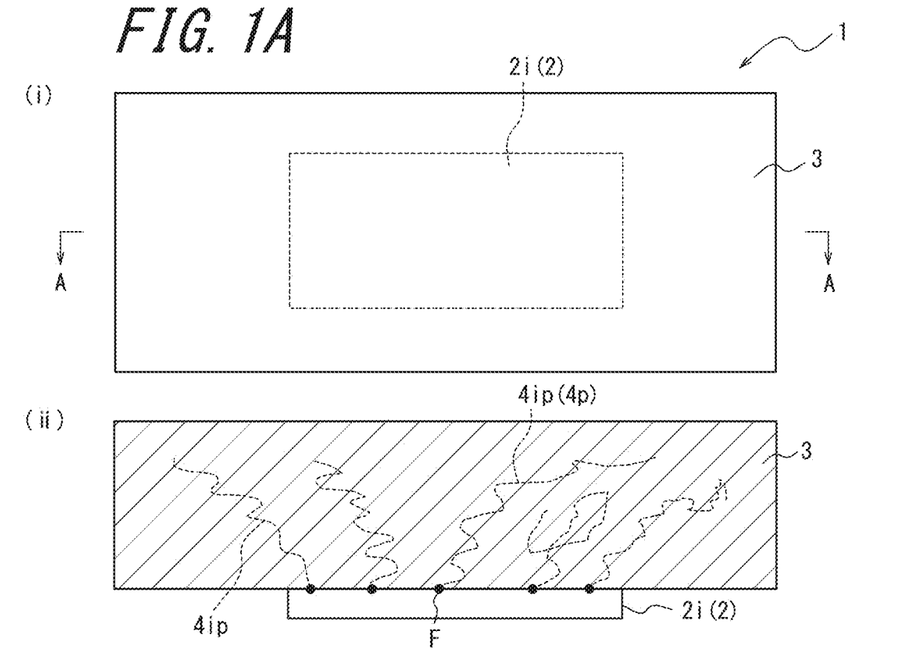
FIGS. 1A and 1B illustrate the composite material of the presently disclosed embodiment, where
(i) of FIG. 1A is a plan view of an example of the presently disclosed composite material,
(ii) of FIG. 1A is a cross-sectional view taken along the Line A-A in (i) of FIG. 1A,
(i) of FIG. 1B is a plan view of another example of the presently disclosed composite material, and
(ii) of FIG. 1B is a cross-sectional view taken along the Line A-A in (i) of FIG. 1B.
Figure 1B:
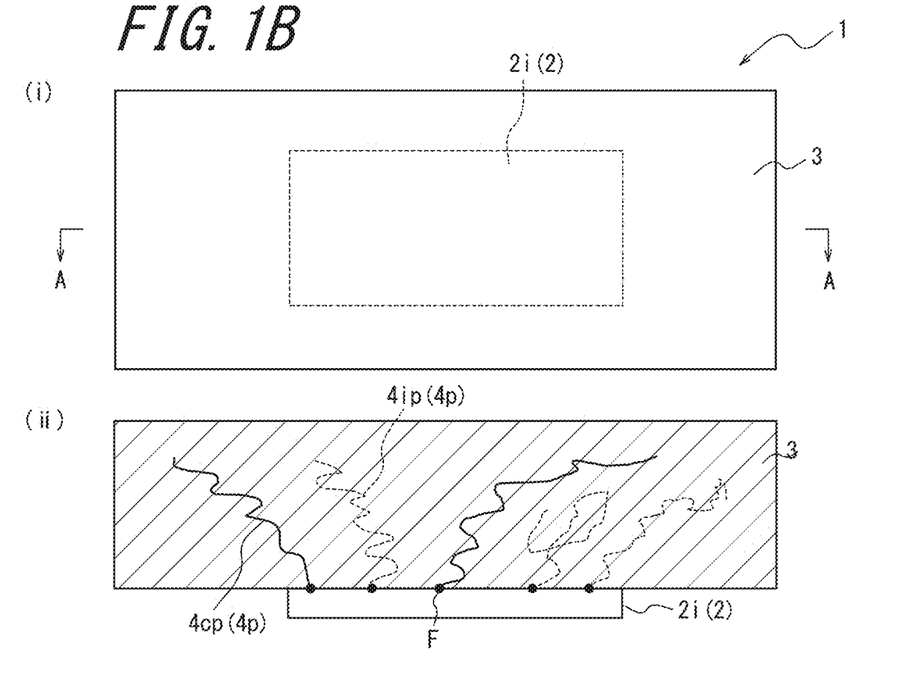

As illustrated in FIGS. 1A and 1B, the composite material 1 of the presently disclosed embodiment includes a substrate 2, a porous body 3 provided on the substrate 2, and insulating polymers 4$ip$ starting from a surface of the substrate 2 and extending inside the porous body 3.

FIGS. 1A and 1B illustrate the cross-sectional view of the composite material of the presently disclosed embodiment. In FIG. 1A, (i) is a plan view of an example of the presently disclosed composite material, and (ii) is a cross-sectional view taken along the Line A-A in (i) of FIG. 1A. In FIG. 1B, (i) is a plan view of another example of the presently disclosed composite material, and (ii) is a cross-sectional view taken along the Line A-A in (i) of FIG. 1B.

For the composite material 1 of the presently disclosed embodiment, the polymers 4$p$, which start from the surface of the substrate 2 and extend inside the porous body 3, may simply be insulating polymers 4$ip$ as illustrated in FIG. 1A, and may optionally include conductive polymers 4$cp$ in addition to the insulating polymers 4$ip$ as illustrated in FIG. 1B.

Figure 3:
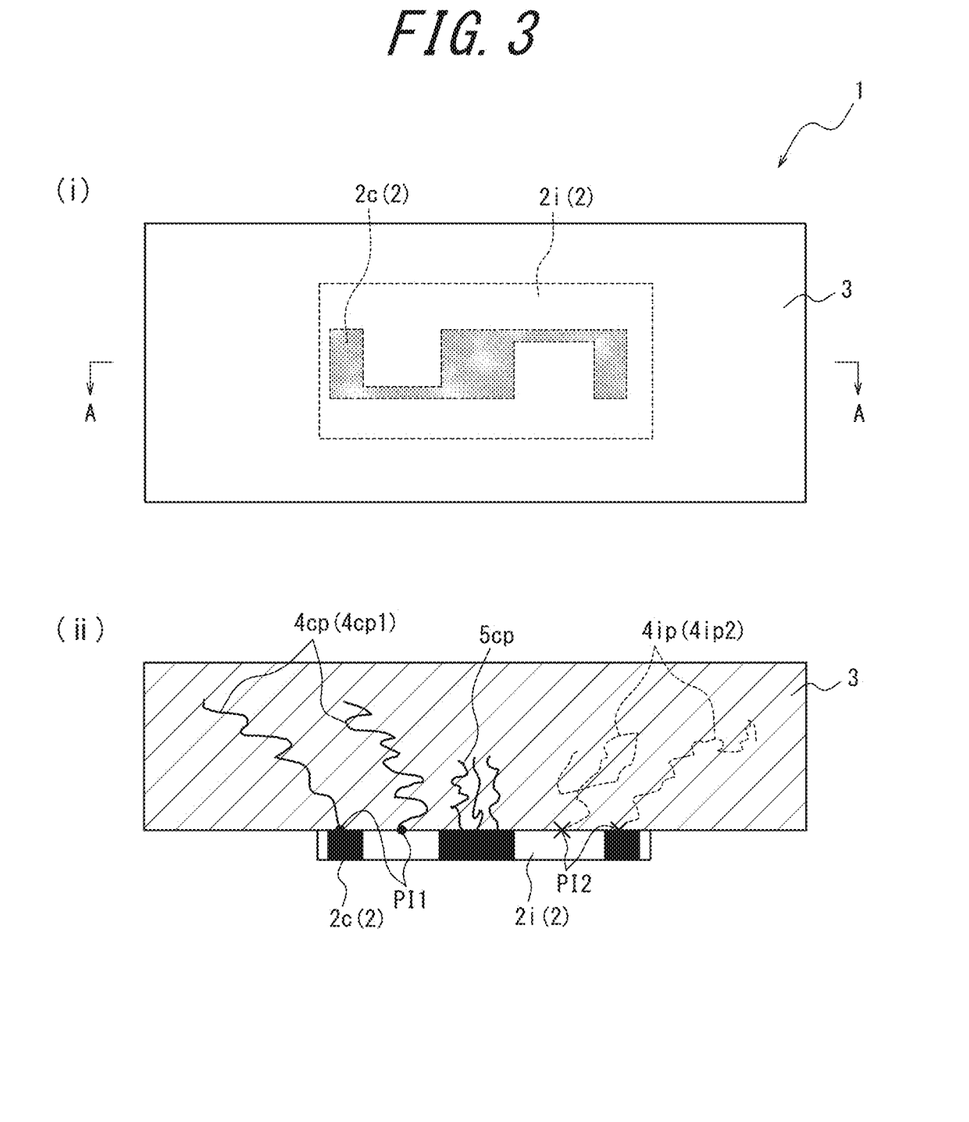
FIG. 3 illustrates a further example of the presently disclosed composite material, where (i) is a plan view thereof and (ii) is a cross-sectional view taken along the Line A-A in (i) of FIG. 3.

Furthermore, the substrate 2 of the composite material 1 of the presently disclosed embodiment may simply be an insulating substrate 2$i$ as illustrated in FIGS. 1A and 1B, and may be a combination of insulating substrate 2$i$ and conductive substrate 2$c$ as illustrated in FIG. 3. FIG. 3 will be described later.

In the drawings, the insulating polymers 4$ip$ are indicated by broken lines while the conductive polymers 4$cp$ are indicated by solid lines, and the insulating substrate 2$i$ is a white portion while the conductive substrate 2$c$ is a black portion (the same applies hereinafter).

Specifically, in order to enhance the adhesion of the substrate 2 to the porous body 3 via the insulating polymers 4$ip$, the porous body 3 of the composite material 1 of the presently disclosed embodiment is preferably provided so as to be in contact (preferably in close contact) with the surface of the substrate 2 as illustrated in FIGS. 1A and 1B.

For the composite material 1 of the presently disclosed embodiment, the insulating polymers 4$ip$ are preferably covalently bonded to foundations F (indicated as black dots in the figures) where one end of the foundation F has been introduced to the surface of the substrate 2 as illustrated in FIGS. 1A and 1B. Additionally, in order to enhance the adhesion of the substrate 2 to the porous body 3, the insulating polymers 4$ip$ preferably extend so as to penetrate into the porous body 3 from one side to the other side in the thickness direction as illustrated in FIGS. 1A and 1B. Furthermore, in order to enhance the adhesion of the substrate 2 to the porous body 3, the insulating polymers 4$ip$ preferably intertwine with the material forming the porous body 3 (e.g. polymers when the porous body 3 is a polymer gel).

The following describes each element of the composite material 1 of the presently disclosed embodiment in detail.

The substrate 2 is not particularly limited as long as the foundations F can be provided on its surface (the foundations F are polymerization initiators PI of polymerization of the insulating polymers 4$ip$ as described later). The substrate 2 may be an insulating substrate 2$i$ or a conductive substrate 2$c$.

A common resin or a resin composition containing such resin can be used as the insulating substrate 2$i$.

Examples of the resin include polyurethane, polypropylene, polylactic acid, poly(lactide-co-glycolide) copolymer, polydioxanone, acrylonitrile-butadiene-styrene copolymer, acrylic ester, acrylonitrile-ethylene-propylene rubber-styrene copolymer, acrylonitrile-styrene copolymer, acrylonitrile styrene acrylate, polybutadiene, bismaleimide triazine, cellulose acetate, cellulose acetate butyrate, cellulose acetate propionate, cyclic butyl terephthalate, cresol formaldehyde, carboxymethyl cellulose, nitrocellulose, hydrin rubber, cellulose propionate, chlorinated vinyl chloride, chloroprene rubber, casein, cellulose triacetate, diallyl phthalate, ethylene-chlorotrifluoroethylene copolymer, ethylenediaminetetraacetic acid, ethylene ethyl acrylate, ethylene methyl acrylate, ethylene methacrylic acid, epoxy resin, ethylene-propylene-diene terpolymer, ethylene-tetrafluoroethylene copolymer, ethylene-vinyl acetate copolymer, ethyl vinyl ether, perfluoro rubber, polyethylene, polystyrene, butyl rubber, isoprene rubber, diphenylmethane isocyanate, melamine formaldehyde, nitrile rubber, polymethyl methacrylate, polyimide, polyethylene terephthalate, polycarbonate, polyether ether ketone, polyisobutylene, polymethyl methacrylate, polystyrene, polyvinyl acetate, polyvinyl chloride, nylon, polyvinylidene fluoride, polyvinyl alcohol, polyvinylpyrrolidone, styrene butadiene, silicone, polyester, Teflon® (Teflon is a registered trademark in Japan, other countries, or both), and polytetrafluoroethylene. From the perspective of biocompatibility and stability, polyurethane, polypropylene, polyethylene, polybutadiene, polymethyl methacrylate, polyethylene terephthalate, polyimide, silicone, polyester, Teflon, and polytetrafluoroethylene are particularly preferable. These materials may be contained alone or in combination of two or more.

Examples of the conductive substrate $2c$ include carbon material, conductive polymer material, semiconductor and metal. The conductive substrate $2c$ can work as an electrode in the composite material $1$.

Examples of the carbon material include carbon nanotube, Ketjen black, glassy carbon, graphene, fullerene, carbon fiber, carbon fabric, and carbon aerogel. Examples of the conductive polymer material include polyaniline, polyacetylene, polypyrrole, poly (3,4-ethylenedioxythiophene), poly (p-phenylenevinylene), polythiophene, and poly (p-phenylene sulfide). Examples of the semiconductor include silicone, germanium, indium tin oxide (ITO), titanium oxide, copper oxide, and silver oxide. Examples of the metal include gold, platinum, silver, titanium, aluminum, tungsten, copper, iron, and palladium.

In particular, the conductive substrate $2c$ is preferably a carbon material, poly (3,4-ethylenedioxythiophene), polypyrrole, gold or platinum from the perspective of electron conductivity, stability and biocompatibility.

These materials may be contained alone or in combination of two or more.

The porous body $3$ is not particularly limited as long as it has a form stability and can be impregnated with monomers $4m$. Examples of the porous body $3$ include sponge, pumice and gel, among which gel is particularly preferable. Note that in this specification, porous body generally includes gel.

Examples of the gel include hydrogel and oily gel, among which hydrogel is particularly preferable.

Examples of hydrogel material (a material that forms a hydrogel when being dispersed in a dispersion medium of water) include natural polymer such as agar, gelatin, agarose, xanthan gum, gellan gum, sclerotia gum, gum arabic, gum tragacanth, karaya gum, cellulose gum, tamarind gum, guar gum, locust bean gum, glucomannan, chitosan, carrageenan, quince seed, galactan, mannan, starch, dextrin, curdlan, casein, pectin, collagen, fibrin, peptide, chondroitin sulfate such as sodium chondroitin sulfate, hyaluronic acid (mucopolysaccharide) and hyaluronate such as sodium hyaluronate, alginic acid and alginate such as sodium alginate and calcium alginate, and their derivatives; cellulose derivative such as methylcellulose, hydroxymethylcellulose, hydroxyethylcellulose, hydroxypropylcellulose, hydroxypropylmethylcellulose and carboxymethylcellulose, and their salts; poly(meth)acrylic acid such as polyacrylic acid, polymethacrylic acid and acrylic acid-methacrylic acid alkyl copolymer, and their salts; synthetic polymer such as polyvinyl alcohol, polymer of polyethylene glycol di(meth)acrylate (PPEGDA, PPEGDM), polyhydroxyethylmethacrylate, polyacrylamide, poly(N,N-dimethylacrylamide), poly(2-acrylamido-2-methylpropanesulfonic acid), poly(N-isopropylacrylamide), polyvinylpyrrolidone, polystyrene sulfonic acid, polyethylene glycol, carboxyvinyl polymer, alkyl-modified carboxyvinyl polymer, maleic anhydride copolymer, polyalkylene oxide resin, crosslinked body of poly(methyl vinyl ether-alt-maleic anhydride) and polyethylene glycol, crosslinked polyethylene glycol, crosslinked N-vinylacetamide, crosslinked acrylamide, and crosslinked starch-acrylate graft copolymer; silicone; interpenetrating network hydrogel and semi-interpenetrating network hydrogel (DN hydrogel); and mixtures of at least two of these.

Among these materials, collagen, glucomannan, fibrin, alginic acid, polyvinyl alcohol, PPEGDA, PPEGDM, polyhydroxyethylmethacrylate, polyvinylpyrrolidone, polyacrylamide, poly(N,N-dimethylacrylamide), poly(N-isopropylacrylamide), silicone, DN hydrogel, and mixtures of at least two of these are preferable from the perspective of obtaining biocompatibility and ease of molding, and from the perspective of enhancing mechanical strength (reducing brittleness).

These materials may be contained alone or in combination of two or more.

The insulating polymers $4ip$ may be the same as or different from the hydrogel material constituting the hydrogel, which is one form of the porous body $3$ as described above.

The insulating polymers $4ip$ are preferably one that can be subjected to a polymerization starting with a photoreaction, thermal reaction or oxidation-reduction reaction, so that the composite material can be easily produced with the method of producing composite material $1$ of the presently disclosed embodiment as described later. Specifically, examples of the insulating polymers $4ip$ include poly(meth)acrylic acid such as polyacrylic acid, polymethacrylic acid and acrylic acid-methacrylic acid alkyl copolymer, and their salts; synthetic polymer such as polymer of polyethylene glycol di(meth)acrylate (PPEGDA, PPEGDM), polyhydroxyethylmethacrylate, polyacrylamide, poly(N,N-dimethylacrylamide), poly(2-acrylamido-2-methylpropanesulfonic acid), poly(N-isopropylacrylamide), polyvinylpyrrolidone, polystyrene sulfonic acid, polyethylene glycol, carboxyvinyl polymer, alkyl-modified carboxyvinyl polymer, maleic anhydride copolymer, polyalkylene oxide resin, crosslinked body of poly(methyl vinyl ether-alt-maleic anhydride) and polyethylene glycol, crosslinked polyethylene glycol, crosslinked N-vinylacetamide, crosslinked acrylamide, and crosslinked starch-acrylate graft copolymer; and silicone. Polyacrylamide, poly(N,N-dimethylacrylamide), PPEGDA and PPEGDM are particularly preferable because they do not deform when the surrounding environment changes (their degree of swelling does not change when the temperature, PH or the like changes). These materials may be contained alone or in combination of two or more.

The insulating polymers $4ip$ may have a conductivity of less than 1 mS/cm, and preferably less than 0.1 mS/cm.

Examples of the conductive polymers $4cp$, which are optionally used in the present disclosure, include poly(3,4-ethylenedioxythiophene), polyacetylene, polypyrrole, polythiophene, polybithiophene, polyisothiophene, polydodecylthiophene, polyisonite thiophene, poly-3-hexylthiophene, polyanion, polyisothianaphthene, polythiazyl, polyphenylene, polyfluorene, polydiacetylene, polyacene, polyparaphenylene, polythienylenevinylene, and polyphenylene sulfide. Poly(3,4-ethylenedioxythiophene) and polypyrrole are particularly preferable from the perspective of electron conductivity and structural stability. These materials may be contained alone or in combination of two or more.

In particular, when the porous body $3$ is a polymer hydrogel and the insulating polymers $4ip$ are a hydrogel material, the composite material $1$ of the present embodiment may be made into a material having no electron conductivity (conductivity), or into a material having ionic conductivity by, for example, containing an electrolyte in the hydrogel.

Furthermore, when the porous body $3$ is a polymer hydrogel and the insulating polymers $4ip$ (as well as the optionally used conductive polymers $4cp$) are a hydrogel material, a polymer layer made of polymers extending from the surface of the substrate $2$ into the porous body $3$ forms inside the porous body $3$ in the composite material $1$.

In this case, the thickness of the polymer layer, which is indicated in a cross-sectional view obtained by cutting the composite material $1$ along the thickness direction, may be 5 μm or more, preferably 10 μm or more, more preferably 100 μm or more, particularly preferably 500 μm or more, and still more preferably more from the perspective of enhancing the adhesive strength of each polymer layer-existing location. Note that the thickness of the polymer layer here refers to the maximum thickness of the polymer layer.

The insulating polymers 4ip and the conductive polymers 4cp may, respectively, have a number average molecular weight (Mn) of 100 or more, preferably 1,000 or more, more preferably $10^4$ or more, particularly preferably $10^5$ or more, and still more preferably more from the perspective of enhancing the adhesive strength.

The number of the foundation F introduced to the surface of the substrate 2 per unit area may be $10^{11}/mm^2$ to $10^{15}/mm^2$, and preferably $10^{12}/mm^2$ to $10^{15}/mm^2$ from the perspective of enhancing the adhesive strength.

(Method of Producing Composite Material)

The method of producing composite material of the presently disclosed embodiment includes: introducing polymerization initiators to a surface of a substrate 2; impregnating monomers 4m into a porous body 3; and performing polymerization to carry out a polymerization reaction of the monomers 4m with the polymerization initiators PI being a polymerization starting point.

Figure 2:
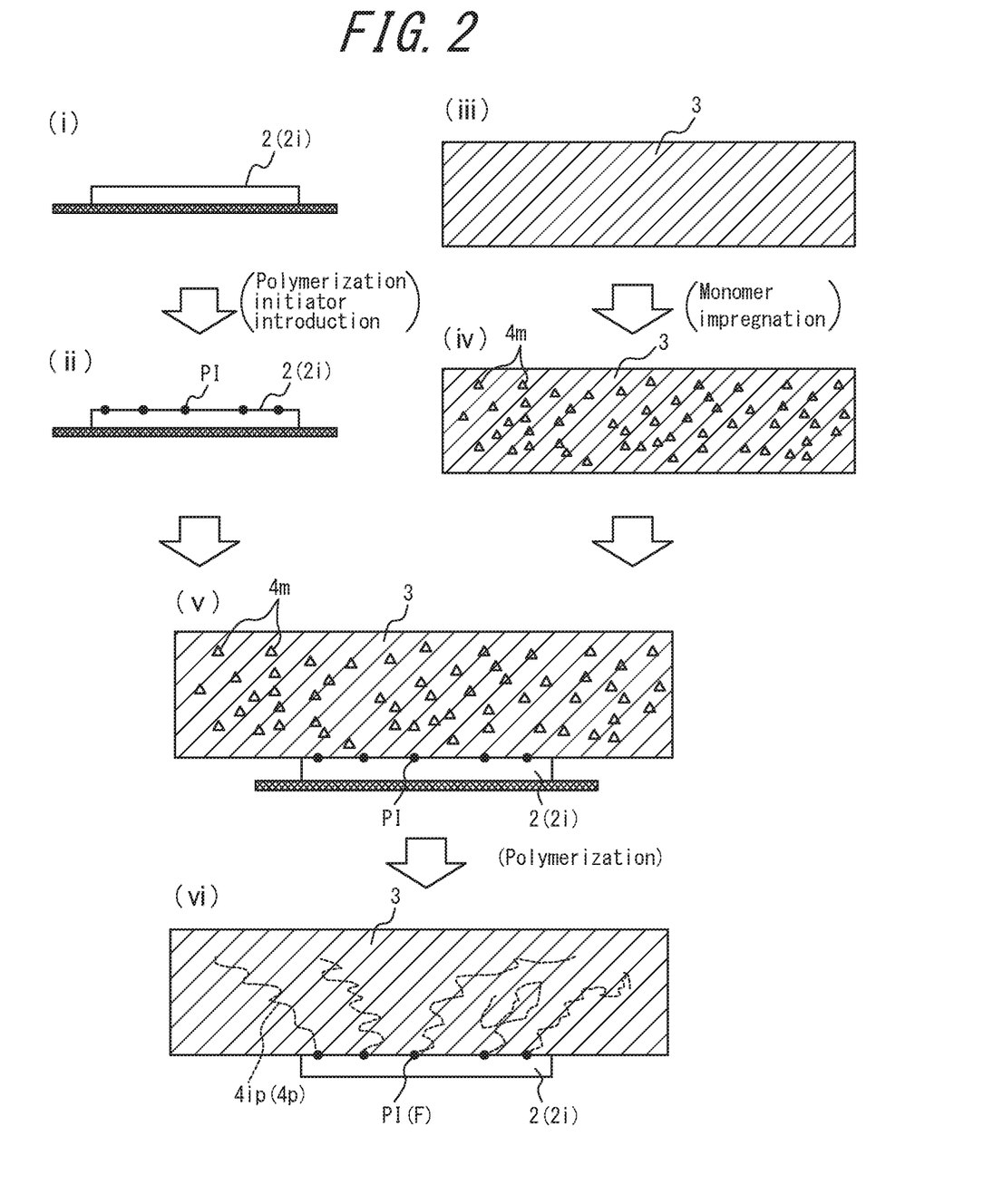
FIG. 2 is an overview of the method of producing composite material of the present embodiment.

FIG. 2 is an overview of the method of producing composite material of the present embodiment. Note that illustrated here is an example of the method of producing the composite material in (i) of FIG. 1A, and the composite material in (i) of FIG. 1A is an example of the presently disclosed composite material.

Through the above process, it is possible to produce the composite material 1 of the present embodiment that includes insulating polymers 4ip starting from the surface of the substrate 2 and extending inside the porous body 3.

The type of the polymerization reaction of the monomers 4m is not particularly limited in the method of producing composite material of the present embodiment. However, the polymerization reaction is preferably a radical polymerization reaction.

[Polymerization Initiator Introduction]

The present embodiment first introduces polymerization initiators PI to the surface of the substrate 2 (see (i) and (ii) of FIG. 2).

Examples of the polymerization initiators PI include alkylphenone type, acylphosphine oxide type, intramolecular hydrogen abstraction type, oxime ester and other types (of Irgacure® (Irgacure is a registered trademark in Japan, other countries, or both) series), benzoin ether type such as isobutyl benzoin ether and isopropyl benzoin ether, benzyl ketal type such as benzyl methyl ketal and hydroxycyclohexyl phenyl ketone, and ketone type such benzophenone and 2-chlorothioxanthone. These materials may be contained alone or in combination of two or more.

The substrate 2 may be the same as the substrate 2 of the composite material 1 of the present embodiment.

The polymerization initiators PI may be introduced by, for example, ozone treatment (introduction of carboxyl group), oxygen plasma treatment, corona discharge treatment, ultraviolet treatment (e.g. introduction of benzophenone), treatment with a silane coupling agent, or treatment with a thiol compound. Additionally, the polymerization initiators PI may be directly introduced by a treatment to the surface of the substrate 2, and may be further bonded via, for example, an ester bond or an amide bond following the treatment.

A specific example of the polymerization initiator introduction is to irradiate ozone to the substrate 2 (e.g. polyurethane) placed on a flat plate and introduce carboxyl groups to the surface of the substrate 2, so that α-hydroxyalkylphenone containing hydroxyl groups can be bound to the carboxyl groups using a condensing agent.

Another example is to coat the surface of the substrate 2 (e.g. polypropylene) placed on a flat plate with benzophenone, so that the benzophenone portion can be introduced to the surface of the substrate 2 by irradiating the coated substrate 2 with ultraviolet rays.

[Monomer Impregnation]

Next, the present embodiment impregnates the porous body 3 with monomers 4m (see (iii) and (iv) of FIG. 2). The monomers 4m here are monomers that can be converted into polymers used as the insulating polymers 4ip.

A specific example of the monomer impregnation is to, when the porous body 3 is a hydrogel, impregnate the hydrogel into an aqueous solution of the monomers 4m.

Another example is to, when the porous body 3 is a polymer hydrogel, impregnate the polymer hydrogel into water to wash (remove) contaminants such as by-products of polymerization reaction and residual monomers, and then impregnate the polymer hydrogel into an aqueous solution of the monomers 4m.

The monomers 4m may be monomers that can be converted into polymers used as the insulating polymers 4ip, and may be monomers that can be converted into polymers used as the conductive polymers 4cp.

The monomers that can be converted into the insulating polymers 4ip may be monomers constituting the above-mentioned insulating polymers 4ip. Examples of the monomers include (meth)acrylic acid such as acrylic acid, methacrylic acid and acrylic acid-methacrylic acid alkyl, and their salts; polyethylene glycol di(meth)acrylate (PEGDA, PEGDM), hydroxyethylmethacrylate, acrylamide, N,N-dimethylacrylamide, 2-acrylamido-2-methylpropanesulfonic acid, N-isopropylacrylamide, vinylpyrrolidone, styrene sulfonic acid, ethylene glycol, maleic anhydride, alkylene oxide, methyl vinyl ether-alt-maleic anhydride, N-vinylacetamide, starch and silanol. Acrylamide, N,N-dimethylacrylamide, PEGDA and PEGDM are particularly preferable, because they do not deform when the surrounding environment changes (their degree of swelling does not change when the temperature, PH or the like changes). These materials may be contained alone or in combination of two or more.

The monomers that can be converted into the conductive polymers 4cp may be monomers constituting the above-mentioned conductive polymers 4cp. Examples of the monomers include 3,4-ethylenedioxythiophene, acetylene, pyrrole, thiophene, bithiophene, isothiophene, dodecylthiophene, isonite thiophene, 3-hexylthiophene, isothianaphthene, thiazyl, fluorene, diacetylene, acene, paraphenylene, thienylenevinylene, and phenylene sulfide. (3,4-ethylenedioxythiophene) and pyrrole are particularly preferable from the perspective of electron conductivity and structural stability. These materials may be contained alone or in combination of two or more.

The porous body 3 may be the same as the porous body 3 of the composite material 1 of the present embodiment.

[Polymerization]

The present embodiment further performs a polymerization reaction of the monomers 4m that starts from the polymerization initiators PI (see (v) and (vi) of FIG. 2). In this polymerization, the insulating polymers 4ip are synthesized.

The initiation reaction of the polymerization of the monomers 4m may be a thermal reaction, a photoreaction, or an oxidation-reduction reaction. A photoreaction is preferable because a photoreaction can be easily controlled. These reactions may be used alone or in combination of two or more.

The conditions of the polymerization initiation reaction can be appropriately determined according to the characteristics of the polymerization initiators PI.

The conditions of the polymerization reaction can be appropriately determined according to the characteristics of the monomers 4m.

The following describes a further example of the presently disclosed composite material with reference to FIG. 3. The composite material is produced with the method of producing composite material of the present embodiment as described above.

The further example of the presently disclosed composite material 1 includes a substrate 2 containing an insulating substrate 2i and a conductive substrate 2c, a porous body 3 provided on the substrate 2, insulating polymers 4ip (4ip2) and conductive polymers 4cp (4cp1) starting from a surface of the insulating substrate 2i and extending inside the porous body 3, and insulating polymers 4ip (4ip2) and conductive polymers 4cp (4cp1) starting from a surface of the conductive substrate 2c and extending inside the porous body 3.

In FIG. 3, (i) is a plan view of the further example of the presently disclosed composite material, and (ii) is a cross-sectional view taken along the Line A-A in (i) of FIG. 3.

The arrangement of the insulating substrate 2i and the conductive substrate 2c of the further example of the presently disclosed composite material 1 may be appropriately determined according to the purpose and application. In particular, the conductive substrate 2c is in an "S" shape in the plan view of FIG. 3.

The further example of the presently disclosed composite material 1 can be produced, for example, with the following producing method.

First, first polymerization initiators PI1 (the black dots in the figure) are introduced to the surface of the insulating substrate 2i and to the surface of the conductive substrate 2c, and second polymerization initiators PI2 (the crosses in the figure) are introduced to the surface of the insulating substrate 2i and to the surface of the conductive substrate 2c (polymerization initiator introduction). Note that the reaction conditions of the polymerization initiation reaction of the first polymerization initiators PI1 and the reaction conditions of the polymerization initiation reaction of the second polymerization initiators PI2 are different from each other. Next, first monomers (not illustrated in the figure) to be polymerized using the first polymerization initiators PI1 are impregnated into the porous body 3 (first monomer impregnation). Then, polymerization reaction of the first monomers starting from the first polymerization initiators PI1 is carried out (first polymerization). The first monomers here are monomers that can be converted into the conductive polymers 4cp, and first polymers 4cp1 (conductive polymers 4cp) are formed through the polymerization.

Here, the substrate 2 and the porous body 3 are impregnated into a solvent to wash (remove), for example, residual first monomers (washing).

Next, second monomers (not illustrated in the figure) to be polymerized using the second polymerization initiators PI2 are impregnated into the substrate 2 and the porous body 3 that have been washed (second monomer impregnation). Then, polymerization reaction of the second monomers starting from the second polymerization initiators PI2 is carried out (second polymerization). The second monomers here are monomers that can be converted into the insulating polymers 4ip, and second polymers 4ip2 (insulating polymers 4ip) are formed through the polymerization.

In the above producing method, it is possible to set a photoreaction as the polymerization initiation reaction of the first polymerization initiators PI1 and a thermal reaction as the polymerization initiation reaction of the second polymerization initiators PI2. It is also possible to set a photoreaction as the polymerization initiation reaction of both of the first polymerization initiators PI1 and the second polymerization initiators PI2 where the wavelength for PI1 is different from the wavelength for PI2.

As illustrated in FIG. 3, the further example of the presently disclosed composite material 1 may include a portion where other conductive polymers 5cp starting from the surface of the conductive substrate 2c and extending inside the porous body 3 are formed through a electrolytic polymerization using the conductive substrate 2c (see the middle of the figure).

When producing a conventional composite material, the adhesion was realized by electrolytic polymerization. Accordingly, a bonding surface between the substrate 2 and the porous body 3 was required to have conductivity, which means the substrate 2 should be a conductive substrate 2c capable of being an electrode and the polymers 4 extending inside the porous body 3 should be conductive polymers 4cp. However, this may cause problems such as leak current during the electrostimulation to a living body, and noise during the measurement of the electric signal of a living body.

On the other hand, the composite material of the presently disclosed embodiment can extend the polymers 4p from the surface of the substrate 2 without relying on the electron conductivity of the substrate 2 or of the polymers 4p. Accordingly, the entire surface of the substrate 2 can be firmly adhered to the porous body 3 even when the substrate 2 is made partly of conductive substrate 2c and partly of insulating substrate 2i. Additionally, the arrangement of the conductive substrate 2c and insulating substrate 2i is free, and accordingly the conductive substrate 2c can expose to the bonding surface with the porous body 3 only at a desired spot where stimulation or measurement occurs.

The composite material of the presently disclosed embodiment can be suitably used for bioelectrical signal measurement such as electrocardiogram, electromyogram and electroencephalogram, and for control of biological functions with electric current.

EXAMPLES

The following further describes the present disclosure in detail with reference to examples. However, the present disclosure is not limited to the following examples in any way.

A. Production of Composite Material

A-1. Reagents and Materials

Polyurethane granule (made by Okada Engineering)
Tetrahydrofuran (made by Wako Pure Chemical)
1-butanol (made by Wako Pure Chemical)
N, N'-methylenebisacrylamide (MBAA) (made by Wako Pure Chemical)
2-oxoglutaric acid (made by Wako Pure Chemical)
2-acrylamido-2-methyl-1-propanesulfonic acid sodium salt (NaAMPS) (made by Sigma-Aldrich)
N, N-dimethylacrylamide (DMAAm) (made by Sigma-Aldrich)
1-ethyl-3-(3-dimethylaminopropyl) carbodiimide hydrochloride (WSC) (made by Dojindo Laboratories)

2-morpholinoethanesulfonic acid, monohydrate (MES) (made by Dojindo Laboratories)

Irgacure 2959 (made by BASF)

4-dimethylaminopyridine (DMAP) (made by Tokyo Chemical Industry)

3,4-ethylenedioxythiophene (EDOT) (Clevious MV2, made by Heraeus)

Iron tosylate solution (pTS·Fe(III)) (Clevious C-B40V2, made by Heraeus)

Collagen film (made by Koken)

Polyethylene glycol diacrylate (PEGDA) (Mn=700, made by Sigma-Aldrich)

2-hydroxy-2-methyl propiophenone (made by Sigma-Aldrich)

Acrylamide (made by Wako Pure Chemical)

A-2. Preparation of Substrate

A-2-1. Preparation of Film (PEDOT·PU/PU-Irgacure), where a Conductive Film (PEDOT·PU) was Insulatively Coated with Polyurethane (PU) and the Coated Polyurethane (PU) was Introduced with Photopolymerization Initiators A-2-1-1. Preparation of PU Film The polyurethane granules were dissolved in the tetrahydrofuran to prepare a 10 wt % polyurethane (PU) solution.

Slide glass was spin coated with the PU solution at 2000 rpm for 30 seconds and then heated on a hot plate at 100° C. for 10 minutes to obtain a PU film.

A-2-1-2. Immobilization of Photopolymerization Initiator on PU Film Surface

The PU film was subjected to ozone treatment for 5 minutes, using a desktop ultraviolet ozone apparatus for surface treating (PL17-110, made by Taiyo Co., Ltd.) with an intensity of 15 mW/cm$^2$, to reform the surface of the film and to introduce carboxyl groups to the surface of the PU film at a density of around $10^{14}$/mm$^2$.

Distilled water was used to prepare a solution for condensation reaction containing 0.2 M of WSC (condensing agent), 50 mM of Irgacure 2959 (photopolymerization initiator), 2.5 mM of DMAP (accelerator of condensation reaction), and 0.1 M of MES.

The PU film, after introducing carboxyl groups, was immersed in the solution for condensation reaction and left at room temperature (25° C.) in the dark overnight. In this way, Irgacure 2959 was immobilized on the surface of the PU film (PU-Irgacure).

A-2-1-3. Preparation of Conductive Film (PEDOT·PU)

35 mL of 10 wt % PU solution, 2 mL of 1-butanol, 0.88 mL of EDOT solution, and 6.5 mL of pTS·Fe(III) were mixed in an ice bath to prepare an EDOT/PU solution.

Slide glass was spin coated with the EDOT/PU solution at 750 rpm for 30 seconds and then heated on a hot plate at 100° C. for 10 minutes to obtain a PEDOT·PU film.

A-2-1-4. Lamination of Photopolymerization Initiator-Immobilized PU Film to PEDOT·PU The PU-Irgacure film was placed on the surface of the PEDOT·PU film and then heated in an oven at 70° C. for 10 minutes. In this way, the two films were laminated together to obtain a PEDOT·PU/PU-Irgacure film.

A-2-2. Preparation of Film (PP-BP), where a Polypropylene Film (PP) was Introduced with Photopolymerization Initiators A PP film was subjected to ultrasonic cleaning with heptane for 10 minutes.

The PP film was immersed in 50 mM of benzophenone (photopolymerization initiator) heptane solution at room temperature (25° C.) in the dark for 1 hour. Next, the PP film was taken out of the solution and dried at room temperature (25° C.) in the dark for 30 minutes. In this way, the benzophenone was adsorbed on the PP film.

The PP film, after adsorbing the benzophenone, was irradiate with ultraviolet (365 nm, intensity: 1 mW/cm$^2$) in a glove box filled with nitrogen. In this way, the benzophenone was chemically immobilized on the surface of the PP film.

A-2-3. Preparation of Film (Glass/PU-Irgacure), where a Glass Plate was Coated with Polyurethane (PU) and the Coated Polyurethane (PU) was Introduced with Photopolymerization Initiators With the same operation as in "A-2-1-1." and in "A-2-1-2.", a PU film was prepared and photopolymerization initiators were immobilized on the surface of the PU film.

Slide glass (size: 15 mm×30 mm) was prepared. With the same operation as in "A-2-1-4.", the slide glass and the photopolymerization initiator-immobilized PU film were laminated together to obtain a glass/PU-Irgacure film.

A-3. Preparation of Porous Body (Hydrogel)

A-3-1. Preparation of Double Network (DN) Hydrogel

Distilled water was used to prepare a first prepolymer solution containing 1 M of NaAMPS (monomer), 40 mM of MBAA (cross-linking agent), and 1 mM of 2-oxoglutaric acid (photopolymerization initiator).

Two glass plates were laminated via a silicone spacer having a thickness of 0.2 mm, and a gap between the plates was filled with the first prepolymer solution.

The glass plates were irradiated with ultraviolet (365 nm, intensity: 1 mW/cm$^2$) in a glove box filled with nitrogen for 6 hours to obtain a (first) PNaAPMS hydrogel.

Next, distilled water was used to prepare a second prepolymer solution containing 3 M of DMAAm (monomer), 3 mM of MBAA, and 1 mM of 2-oxoglutaric acid.

The (first) PNaAPMS hydrogel was immersed in the second prepolymer solution for 2 days, and then irradiated with ultraviolet (365 nm, intensity: 1 mW/cm$^2$) in a glove box filled with nitrogen for 6 hours. In this way, a DN hydrogel was obtained where PNaAPMS and PDMAAm had interpenetrated each other.

The DN hydrogel was washed with distilled water overnight to remove unreacted monomers and photopolymerization initiators.

A-3-2. Preparation of PPEGDA Hydrogel 0.5 vol % 2-hydroxy-2-methyl propiophenone (photopolymerization initiator) was dissolved in a 20 vol % PEGDA aqueous solution to prepare a polymerization solution.

Two ultraviolet-transparent acrylic plates were laminated via a silicone spacer having a thickness of 1 mm, and a gap between the plates was filled with the polymerization solution.

The acrylic plates were irradiated with ultraviolet (365 nm, intensity: 1 mW/cm$^2$) for 1 minute to obtain a PPEGDA hydrogel.

The PPEGDA hydrogel was washed with distilled water overnight to remove unreacted monomers and photopolymerization initiators.

In addition to the above, a collagen hydrogel was also prepared.

A-4. Preparation of Composite Material

A-4-1. Adhesion of Hydrogel (DN, Collagen, or PPEGDA) to Film (PEDOT·PU/PU-Irgacure)

A subject hydrogel was immersed in a PBS solution (prepolymer solution for adhesion) containing 50 wt % acrylamide for at least 1 hour. A DN hydrogel, a collagen gel hydrogel, or a PPEGDA hydrogel was used for the hydrogel. In particular, 0.06 mol % MBAA was added to the prepolymer solution for adhesion when using a collagen hydrogel.

The PEDOT·PU/PU-Irgacure film was processed into an arbitrary design, and the subject hydrogel was laminated to the surface of the film.

The film-hydrogel laminate was sandwiched between two ultraviolet-transparent acrylic plates, and the whole package was wrapped in Saran Wrap® (Saran Wrap is a registered trademark in Japan, other countries, or both).

The package, while being introduced with nitrogen, was irradiated with ultraviolet (302 nm, intensity: 370 µW/cm$^2$) for 6 minutes to make polyacrylamides for adhesion extend from the surface of the PU film into the hydrogel. The number average molecular weight (Mn) of the polyacrylamide was estimated to be around $10^6$.

The film-hydrogel laminate, after the ultraviolet irradiation, was taken out of the acrylic plates to obtain a composite material where the PEDOT·PU/PU-Irgacure film and the hydrogel had been adhered together via the polyacrylamides.

A-4-2. Adhesion of Hydrogel to PP Film

A subject hydrogel was immersed in a PBS solution (adhesive prepolymer solution) containing 50 wt % acrylamide for at least 1 hour. A PPEGDA hydrogel was used for the hydrogel.

The PPEGDA hydrogel was laminated to the surface of the PP-BP film.

The film-hydrogel laminate was sandwiched between two ultraviolet-transparent acrylic plates, and the whole package was wrapped in Saran Wrap®.

The package, while being introduced with nitrogen, was irradiated with ultraviolet (365 nm, intensity: 1 mW/cm$^2$) for 10 minutes to make polyacrylamides for adhesion extend from the surface of the PP film into the hydrogel.

The film-hydrogel laminate, after the ultraviolet irradiation, was taken out of the acrylic plates to obtain a composite material where the PP-BP film and the PPEGDA hydrogel had been adhered together via the polyacrylamides.

A-4-3. Adhesion of Hydrogel to Glass/PU-Irgacure

A subject hydrogel (size: 15 mm×30 mm) was immersed in a phosphate buffer solution (adhesive prepolymer solution) containing 50 wt % acrylamide for at least 1 hour. A DN hydrogel was used for the hydrogel.

The glass/PU-Irgacure and the DN hydrogel were placed together so that they were partly in contact with each other. Specifically, the glass/PU-Irgacure and the DN hydrogel, both having a width of 15 mm, were overlapped with each other in width so that they were placed together with a contact area being 15 mm×6 mm.

Next, with the same operation as in "A-4-1.", the glass/PU-Irgacure and the DN hydrogel were irradiated with ultraviolet (365 nm, intensity: 1 mW/cm$^2$) for 6 minutes. In this way, the acrylamide was photopolymerized and a composite material was obtained where the glass/PU-Irgacure and the DN hydrogel had been adhered together via polyacrylamides.

Figure 7:
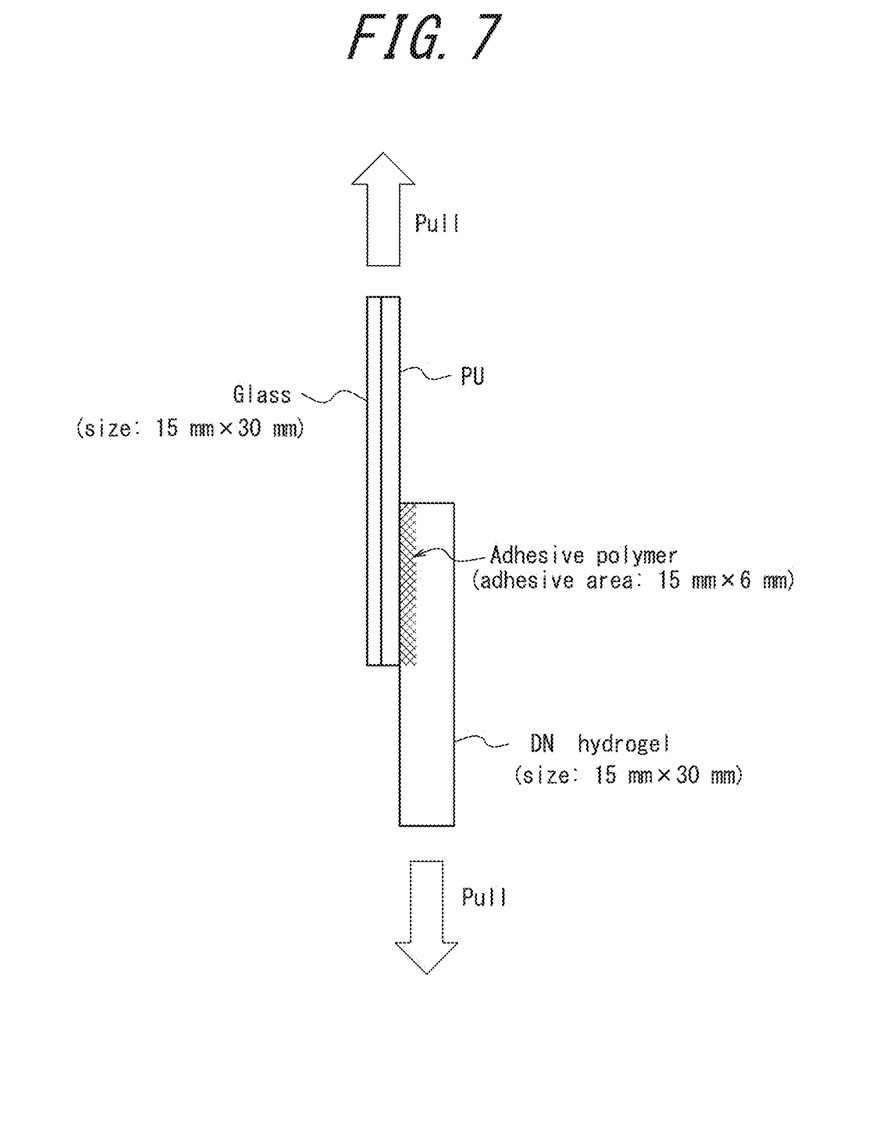
FIG. 7 is a cross-sectional view of a composite material when subjecting it to adhesive strength evaluation, where the composite material is obtained in "A-4-3." of the Examples by adhering a DN hydrogel to a glass/PU-Irgacure via polyacrylamides.

FIG. 7 is a cross-sectional view of a composite material when subjecting it to adhesive strength evaluation, where the composite material is obtained in "A-4-3." of the Examples by adhering a DN hydrogel to a glass/PU-Irgacure via polyacrylamides.

B. Structural Analysis and Property Evaluation

Figure 4A:
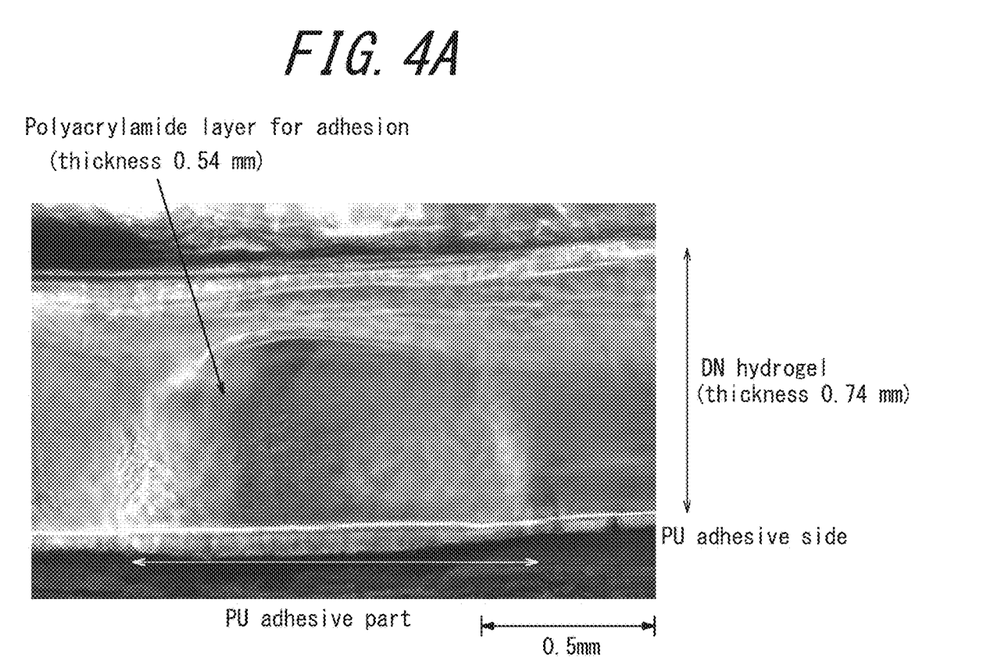
Figure 4B:
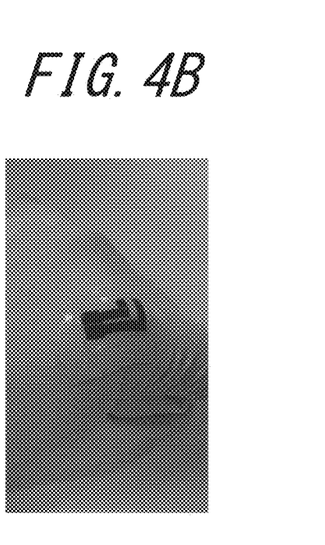
Figure 4C:
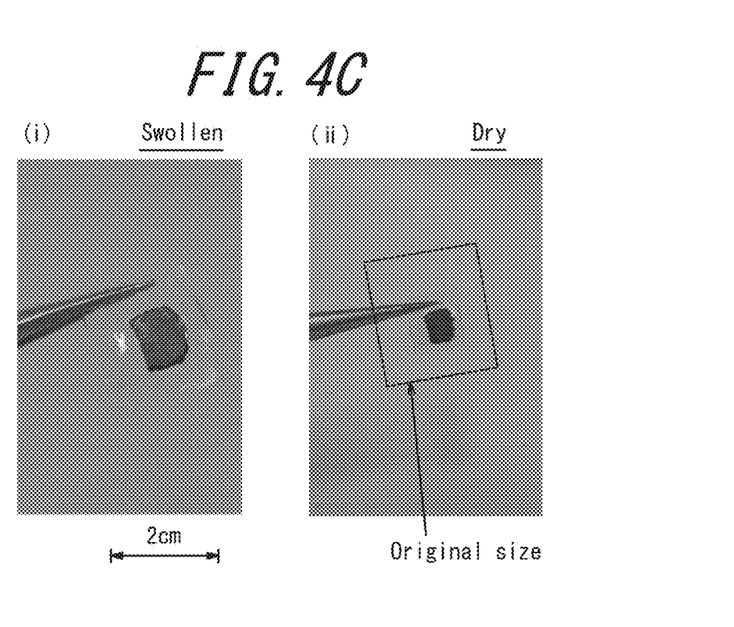

FIG. 4A-4C are photographs when observing a composite material with the naked eye or with an inverted microscope, where the composite material is obtained by adhering a DN hydrogel to a PEDOT·PU/PU-Irgacure film.

FIG. 4A is a photograph when observing the composite material with an inverted microscope.

As illustrated in FIG. 4A, a section (the shadow), which was a semicircular portion in the cross-sectional view extending from the surface of the PEDOT·PU/PU-Irgacure film adhesive part (indicated by a white double-pointed arrow at the bottom of the photograph) into the DN hydrogel, was observed. The section (the shadow) was observed as a portion partitioned from the surrounding DN hydrogel, which may be caused by the different refractive indexes of the hydrogel inside and outside the partition.

The fact that no shadow was observed outside the PU adhesive part suggested the existence of a polyacrylamide portion (polyacrylamide layer) starting from the surface of the PEDOT·PU/PU-Irgacure film and extending inside the DN hydrogel.

According to the photograph, the thickness of the DN hydrogel was 0.74 mm and the thickness of the polyacrylamide layer was 0.54 mm.

As described above, the polyacrylamides realized a firm adhesion between the PEDOT·PU/PU-Irgacure film and the DN hydrogel.

FIG. 4B is a photograph when observing the composite material with the naked eye.

For a composite material prepared by using a DN hydrogel in the above-mentioned "A-4-1.", the PEDOT·PU/PU-Irgacure film was adhered to the DN hydrogel so that the film would not peel off even being strongly scratched by tweezers (not illustrated in the figure). Additionally, the hydrogel was flexible enough to be flattened on the back of the hand, as illustrated in FIG. 4B.

In FIG. 4C, (i) is a photograph when observing the composite material with the naked eye, where the composite material is swollen with phosphate buffer solution. In FIG. 4C, (ii) is a photograph when observing the composite material with the naked eye, where the composite material is dry.

As illustrated in FIG. 4C, the PEDOT·PU/PU-Irgacure film peeled off from the hydrogel neither when the composite material swelled to a larger size nor when the composite material shrunk to about half its size because of dryness. Additionally, the fact that even a repeated cycle of drying and swelling did not cause any peeling demonstrated a firm adhesion between the PU film and the DN hydrogel.

Figure 5A:
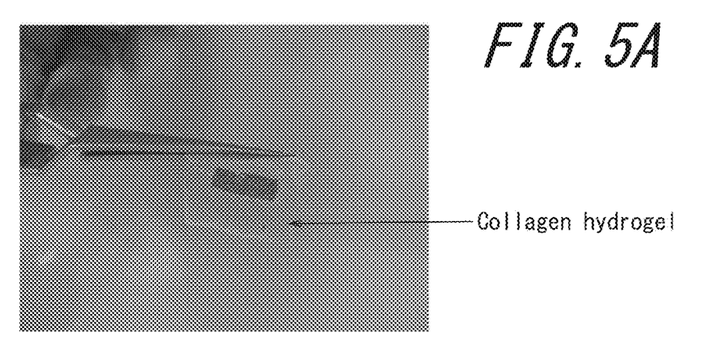
FIG. 5A is a photograph when observing a composite material, which is obtained by adhering a collagen hydrogel to a PEDOT·PU/PU-Irgacure film, with the naked eye.
Figure 5B:
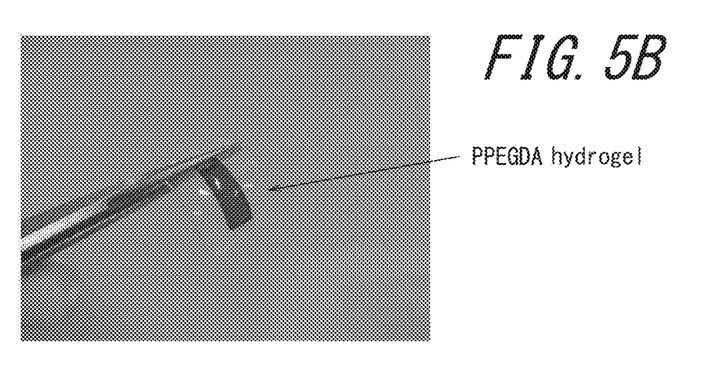
FIG. 5B is a photograph when observing a composite material, which is obtained by adhering a PPEGDA hydrogel to a PEDOT·PU/PU-Irgacure film, with the naked eye.

FIG. 5A is a photograph when observing a composite material with the naked eye, where the composite material is obtained by adhering a collagen hydrogel to a PEDOT·PU/PU-Irgacure film. FIG. 5B is a photograph when observing a composite material with the naked eye, where the composite material is obtained by adhering a PPEGDA hydrogel to a PEDOT·PU/PU-Irgacure film.

As illustrated in FIG. 5A, the adhesion between the film and the hydrogel was confirmed in both cases of using collagen hydrogel and using PPEGDA hydrogel, like the case of using DN hydrogel. This suggested that the present disclosure was able to change the type of hydrogel according to the application.

Figure 6:
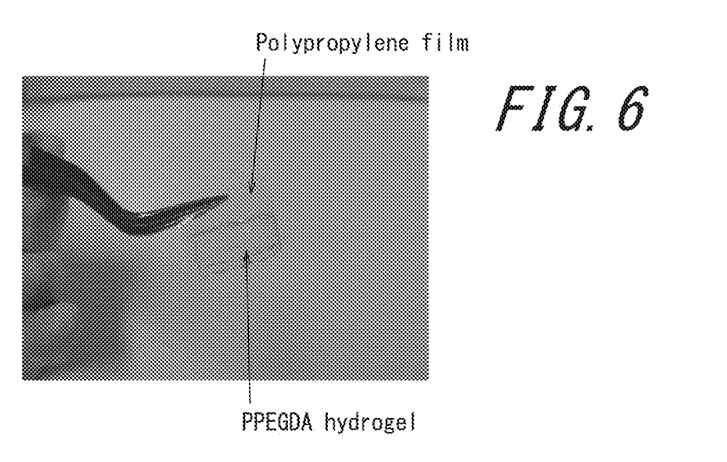
FIG. 6 is a photograph when observing a composite material, which is obtained by adhering a PPEGDA hydrogel to a PP-BP film, with the naked eye.

FIG. 6 is a photograph when observing a composite material with the naked eye, where the composite material is obtained by adhering a PPEGDA hydrogel to a PP-BP film.

As illustrated in FIG. 6, the adhesion between the film and the hydrogel was confirmed in the case of using PP-BP film, like the case of using PEDOT·PU/PU-Irgacure film. This suggested that in the present disclosure, the photopolymerization initiators to be used were not particularly limited and could be appropriately selected C. Adhesive Strength Measurement A shearing test was conducted on the composite material obtained in "A-4-3."

Specifically, two sides of the composite material, the side where the glass/PU-Irgacure protruded and the side where the DN hydrogel protruded, were pulled apart at a speed of 9.3 mm/min using a tensile tester (the DPU made by IMADA), and the stress on which the adhesive part peeled off was measured. The value obtained by dividing the stress by the contact area was defined as the adhesive strength (in unit of kPa). The shearing test was conducted three times, and the average value of the adhesive strength values was calculated. As a result, the average value was 66 kPa.

INDUSTRIAL APPLICABILITY

The present disclosure can provide a composite material where a substrate and a porous body are firmly adhered via insulating polymers. The presently disclosed composite material can be suitably used for bioelectrical signal measurement such as electrocardiogram, electromyogram and electroencephalogram, and for control of biological functions with electric current.

REFERENCE SIGNS LIST 1 composite material
2 substrate
2$i$ insulating substrate
2$c$ conductive substrate
porous body
4$p$ polymer
4$ip$ insulating polymer
4$cp$ conductive polymer
4$m$ monomer
5$cp$ other conductive polymer
F foundation introduced to the surface of the substrate
PI polymerization initiator

The invention claimed is:

1. An electrode for bioelectrical signal measurement or for application of electric current comprising a conductive substrate, an insulating substrate on the conductive substrate, a hydrogel provided on the insulating substrate, and insulating polymers starting from a surface of the insulating substrate and extending inside the hydrogel.

2. The electrode of claim 1, wherein the insulating polymers have a conductivity of less than 1 mS/cm.

3. The electrode of claim 1, wherein the insulating polymers are at least one selected from the group consisting of polyacrylamide, poly(N,N-dimethylacrylamide), PPEGDA and PPEGDM.

4. The electrode of claim 1, wherein the hydrogel is at least one selected from the group consisting of collagen, glucomannan, fibrin, alginic acid, polyvinyl alcohol, PPEGDA, PPEGDM, polyhydroxyethylmethacrylate, polyvinylpyrrolidone, polyacrylamide, poly(N,N-dimethylacrylamide), poly(N-isopropylacrylamide), silicone, DN hydrogel and mixtures of at least two of these.

5. The electrode of claim 1, wherein the conductive substrate comprises conductive polymer material.

6. A method of producing the electrode of claim 1 comprising:
introducing polymerization initiators to a surface of the insulating substrate;
impregnating monomers into hydrogel; and
performing polymerization to carry out a polymerization reaction of the monomers with the polymerization initiators being a polymerization starting point.

7. The method of producing an electrode of claim 6, wherein the polymerization reaction of the monomers is a radical polymerization reaction.

8. The method of producing an electrode of claim 6, wherein the polymerization of the monomers starts with at least one selected from the group consisting of thermal reaction, photoreaction, and oxidation-reduction reaction.

* * * * *